(12) United States Patent
Kurozumi et al.

(10) Patent No.: US 6,833,918 B2
(45) Date of Patent: Dec. 21, 2004

(54) LIGHT SCATTERING PARTICLE SIZE DISTRIBUTION MEASURING APPARATUS AND METHOD OF USE

(75) Inventors: Takuji Kurozumi, Kyoto (JP); Yoshiaki Togawa, Kyoto (JP)

(73) Assignee: Horiba Ltd., Osaka (JP)

( * ) Notice: Subject to any disclaimer, the term of this patent is extended or adjusted under 35 U.S.C. 154(b) by 319 days.

(21) Appl. No.: 09/974,659

(22) Filed: Oct. 9, 2001

(65) Prior Publication Data

US 2002/0041376 A1 Apr. 11, 2002

(30) Foreign Application Priority Data

Oct. 11, 2000 (JP) ........................................ 2000-310610

(51) Int. Cl.[7] .............................................. G01N 15/02
(52) U.S. Cl. ........................................ 356/336; 356/337
(58) Field of Search ................................ 356/335, 336, 356/337–343; 250/216, 574, 573

(56) References Cited

U.S. PATENT DOCUMENTS

| | | | | |
|---|---|---|---|---|
| 5,007,737 A | * | 4/1991 | Hirleman, Jr. ............... | 356/336 |
| 5,576,827 A | * | 11/1996 | Strickland et al. ........... | 356/336 |
| 5,818,583 A | * | 10/1998 | Sevick-Muraca et al. ... | 356/336 |
| 5,936,729 A | * | 8/1999 | Igushi .......................... | 356/336 |
| 6,061,131 A | * | 5/2000 | Igushi et al. ................. | 356/336 |
| 6,091,492 A | * | 7/2000 | Strickland et al. ........... | 356/336 |
| 6,177,994 B1 | * | 1/2001 | Watson et al. ............... | 356/343 |
| 6,236,458 B1 | * | 5/2001 | Igushi et al. ................. | 356/336 |

* cited by examiner

Primary Examiner—Gregory J Toatley, Jr.
Assistant Examiner—Willie Davis
(74) Attorney, Agent, or Firm—Brian F. Swienton (57) ABSTRACT

The present invention provides a light scattering particle size distribution measuring apparatus, which does not require a burdensome optical axis adjustment of operator for every measurement and which is capable of maintaining a state most suitable for measuring.

In the present invention, the light scattering particle size distribution measuring apparatus irradiates a sample with light from a light source, detects the resulting scattered light from the sample by a photodetector. Thereafter, the present invention calculates the size distribution of particles in the sample on the basis of the scattered light intensity pattern obtained. In addition, an automatic adjustment mechanism aligns and maintains the central position of the foregoing photodetector with the central position of the foregoing light source.

10 Claims, 7 Drawing Sheets

LIGHT SCATTERING PARTICLE SIZE DISTRIBUTION MEASURING APPARATUS AND METHOD OF USE

FIELD OF THE INVENTION

The present invention relates to a light scattering particle size distribution measuring apparatus, which irradiates a material sample with light from a light source, and measures the size distribution of particles in the sample on the basis of a scattered light intensity pattern obtained thereat.

DESCRIPTION OF THE PRIOR ART

Figure 7:
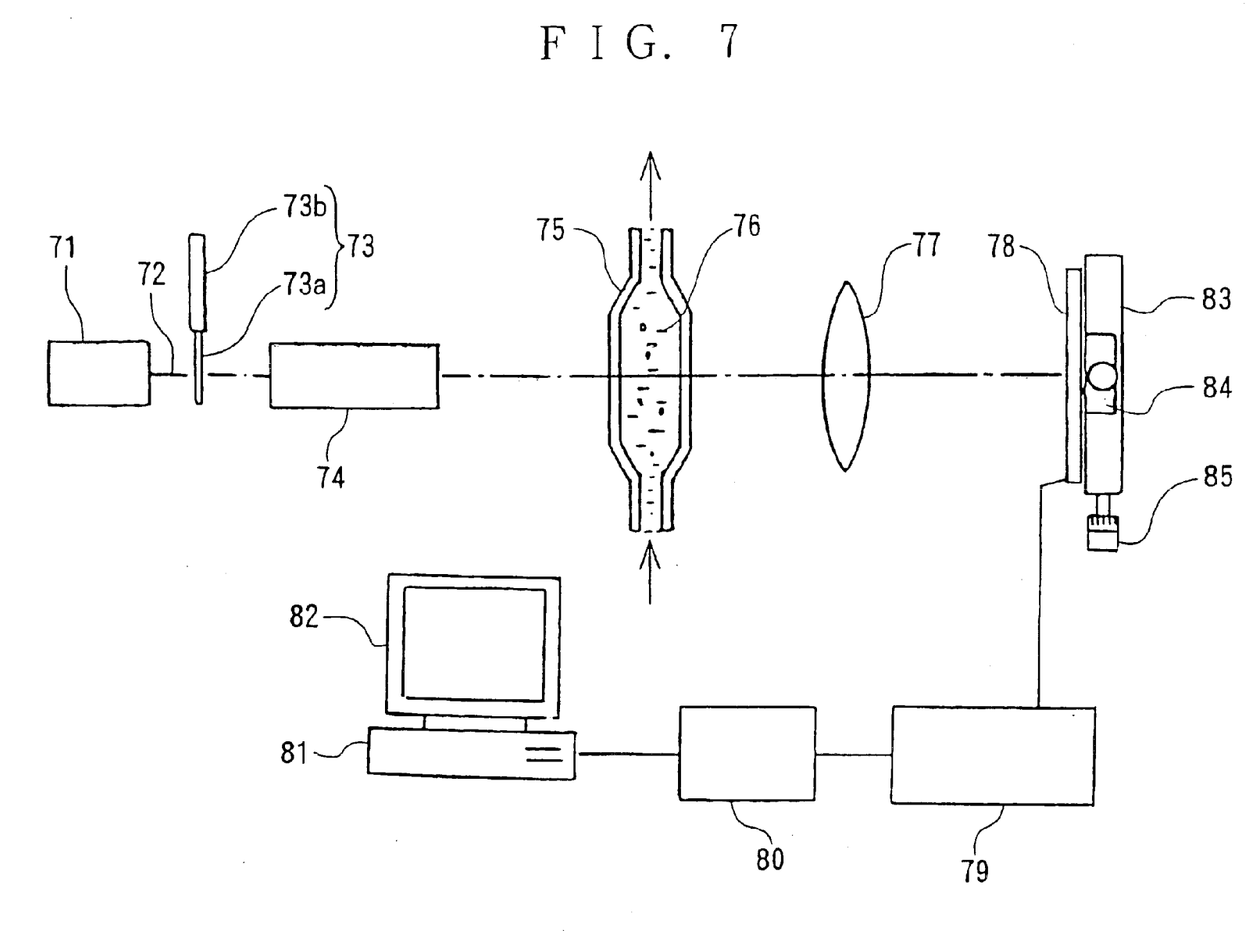
FIG. 7 is a view to illustrate a prior art system.

Systems capable of measuring the size distribution of particles within a sample of material are useful in a plurality of fields. FIG. 7 shows a schematic of a prior art scattering particle size distribution measuring apparatus system. As shown in FIG. 7, the system comprises a light source 71, capable of emitting laser light 72. In addition, a shutter 73, comprising a shutter member 73a and a shutter driving member 73b, is used to modulate the laser light 72. A beam expander 74 expands the laser light 72 prior to incurring a flow through cell 75 containing a material sample 76. Thereafter, a condenser lens 77 is used to focus the light onto a photodetector 78 which detects the scattered and transmitted light from the condensor lens 77. Commonly, a multiplexer 79, which is in communication with a CPU 80, captures the signal from the photodetector 78 upon the detection of light. The CPU 80 may be programmed with various algorithms and other mathematical formulae to permit arithmetic computations of scattering based on the light intensity pattern received at the photodetector 78. A personal computer 81, in communication with a display terminal 82, may be used to control the overall system.

In the foregoing system, when a cell 75 containing a material sample 76 is irradiated with laser light 72, a portion of light is scattered by particles within the material sample 76, and a portion of the light is transmitted through the material without a scattering effect.

A problem associated with prior art systems requires the optical axis of a photodetector 78 be held exactly coincident with that of a light source 71. More specifically, the center of an axis of laser light 72 emitted from a light source 71 is required to be coincident with a center of a light receiving device of the photodetector 78. Commonly, the foregoing axis become misaligned due to the thermal deformation of the light source 71, the thermal deformation of the optical bench, thermal deformations in the cell 75, condenser lens 76, or photodetector 78.

In an effort to correct the foregoing misalignment issues, conventional particle size distribution measuring systems having utilized optical stages 83, commonly referred to as X-Y stages, to maintain the optical axis. As shown in FIG. 7, the X-Y stage moves a photodetector 78 in parallel, and corrects the foregoing misalignment of the optical axis. To correct a misalignment, the operator is required to manually actuate the direct acting actuator 85, to correct misalignment along the X axis, or the direct acting actuator 84, to correct a misalignment along the Y axis. Generally, the direct acting actuators 84 and 85, respectively, having included piezoelectric devices or a stepping motor.

The above-referenced optical axis adjustment work is required to be performed for every measurement and takes several minutes for each adjustment. As such, it has been required for an operator to expend considerable time and effort for each measurement. In addition, inaccurate measurements could occur should there be a time lag between the optical axis adjustment work and the measuring operation due to a plurality of factors, such as, for example, vibrations, changes in temperature, or other environmental conditions.

The present invention has been made in view of the foregoing matters, and an object of the present invention is to provide a light scattering particle size distribution measuring apparatus which does not require a burdensome optical axis adjustment of operator for every measurement, thereby maintaining a state most suitable for measuring.

SUMMARY OF THE INVENTION

To achieve the above object, the present invention discloses a light scattering particle size distribution measuring apparatus which irradiates a sample with light from a light source, detects the resulting scattered light from the sample by a photodetector, and measures the size distribution of particles in the sample on the basis of a scattered light intensity pattern obtained. More specifically, the present invention comprises an automatic adjustment mechanism which aligns and maintains a central position of the foregoing photodetector with a central position of the foregoing light source is provided.

In another embodiment, a light scattering particle size distribution measuring apparatus is provided comprising an optical axis adjustment mechanism capable of automatically adjusting the central positions of the light source and the photodetector in a state most suitable for measuring. The system monitors the quantity of light antecedent to irradiating a sample and quantity of light on a photodetector after irradiating a sample, and adjusts the position of a light source, the photodetector, or an optical device positioned between the light source and the photodetector.

In yet another embodiment, the present invention discloses a light scattering particle size distribution measuring apparatus capable of holding the control data antecedent to the decrease of the quantity of light when the quantity of light on a photodetector is significantly lowered compared with the quantity of light antecedent to irradiating a sample by monitoring the quantity of light antecedent to irradiating a sample and the quantity of light on a photodetector. In addition, the present embodiment is capable of retrieving the optimal positions of various optical components in a range, thereby automatically controlling the quantity of light on a photodetector.

In the light scattering particle size distribution measuring apparatus having the constitution described above, an automatic adjustment mechanism aligns the central position of the photodetector with the central position of the light source. The optical axis adjustment, which, conventionally was required to be manually performed by the operator, or through a control software stored on the personal computer, before measuring the particle size, becomes unnecessary. It is, therefore, possible to reduce the time required for each measurement, such as preparatory work before measuring. In addition, the present system is capable of always measuring in optimal conditions, thereby consistently achieving a particle size distribution measurement having a high degree of measuring precision.

DETAILED DESCRIPTION OF THE PREFERRED EMBODIMENTS

Figure 1:
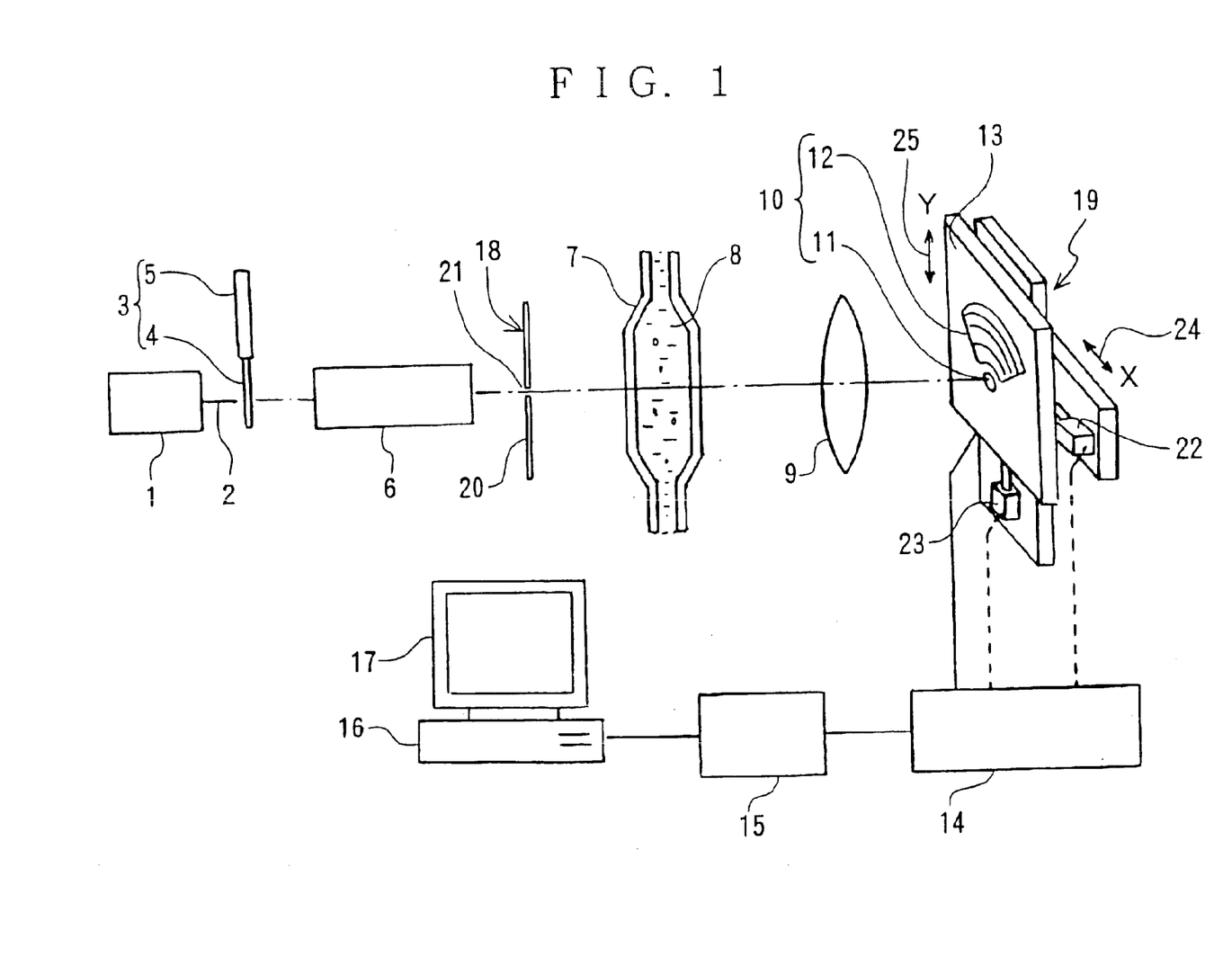
FIG. 1 is a view showing a first embodiment of the present invention.

FIG. 1 shows a first embodiment of the present invention. As shown in FIG. 1, the particle size measuring system comprises a light source 1 capable of emitting laser light 2. The quantity of light emitted from this light source 1 is controlled and monitored by a CPU 15 described herein. The laser light 2 is modulated by a light shutter 3, which comprises a shutter member 4 and a shutter driving member 5. Thereafter, a beam expander 6 expands laser light 2 emitted from the light source 1. The laser light 2 continues through a flow-through cell 7 containing a material sample 8, and is focused with a condenser lens 9 onto a photodetector 10. In an alternate embodiment, the condenser lends 9 may be between the beam expander 6 and the cell 7, thereby condensing the laser light 2 incident upon the sample 8. The photodetector detects 10 comprises a light receiving device 11 having a plurality of arc-shaped receiving devices 12 located an appropriate distance from the center of the optical axis. The foregoing light receiving devices 11 and 12 comprise and may include a plurality of light receiving device known in the art, including, for example, photodiodes. The light receiving devices 11 and 12 may be positioned at a predetermined position on a base member 13. A multiplexer 14 captures the signal from the photodetector 10. The CPU 15 processes the signal from the multiplexer 14 and determines the particle size distribution by performing arithmetic computations on the basis of a scatter light intensity pattern. Thereafter, a personal computer 16 may be used for controlling arithmetic computations, controlling the measuring apparatus, and performing image processing functions. A display unit 17, in communication with the personal computer 16, may be used to display the computational results.

As shown in FIG. 1, a diffraction device 18, capable of producing diffracted light, is inserted into the optical path of the propagating laser light 2. The diffraction device 18 comprises a plate member 20, having a central opening 21 formed therein. Those skilled in the art will appreciate the diffraction device 18 of the present invention may be inserted into the optical path manually, or if desired, independently with an appropriate mechanism. The plate member 20 of the present invention may be manufactured from a plurality of materials, including, for example, light extinction materials and light absorbing materials. In an alternate embodiment, a transparent plate member 20 having light absorption material centrally located thereon, thereby enabling the user to produce spherical particle diffraction.

FIG. 1 shows an adjusting mechanism 19 which comprises, for example, an X-Y stage capable of movement in two directions X and Y, orthogonal to each other. As shown, the photodetector 10 is positioned on the X-Y stage 19. Directional actuators 22 and 23 may be used to drive the X-Y stage 19 in X direction (a direction indicated by an arrow 24) and Y direction (a direction indicated by an arrow 25), respectively. The directional actuators 22 and 23 may comprise direct-acting actuators such as a piezoelectric device or a stepping motor. As shown in FIG. 1, the directional actuators 22 and 23 are controlled by a signal from a personal computer 16. In an alternate embodiment, a manually controlled adjustment mechanism 19 is contemplated.

Those skilled in the art will appreciate the present invention is greatly different from the prior art systems in that the diffraction device 18, which is positionable within the propagation path of the laser light 2, is capable of adjusting the optical axis in the optical path between the light source 1 and the photodetector 10. In addition, further adjustments to the optical axis may be achieved with the adjusting mechanism 19 coupled to the photodetector 10.

Figure 2:
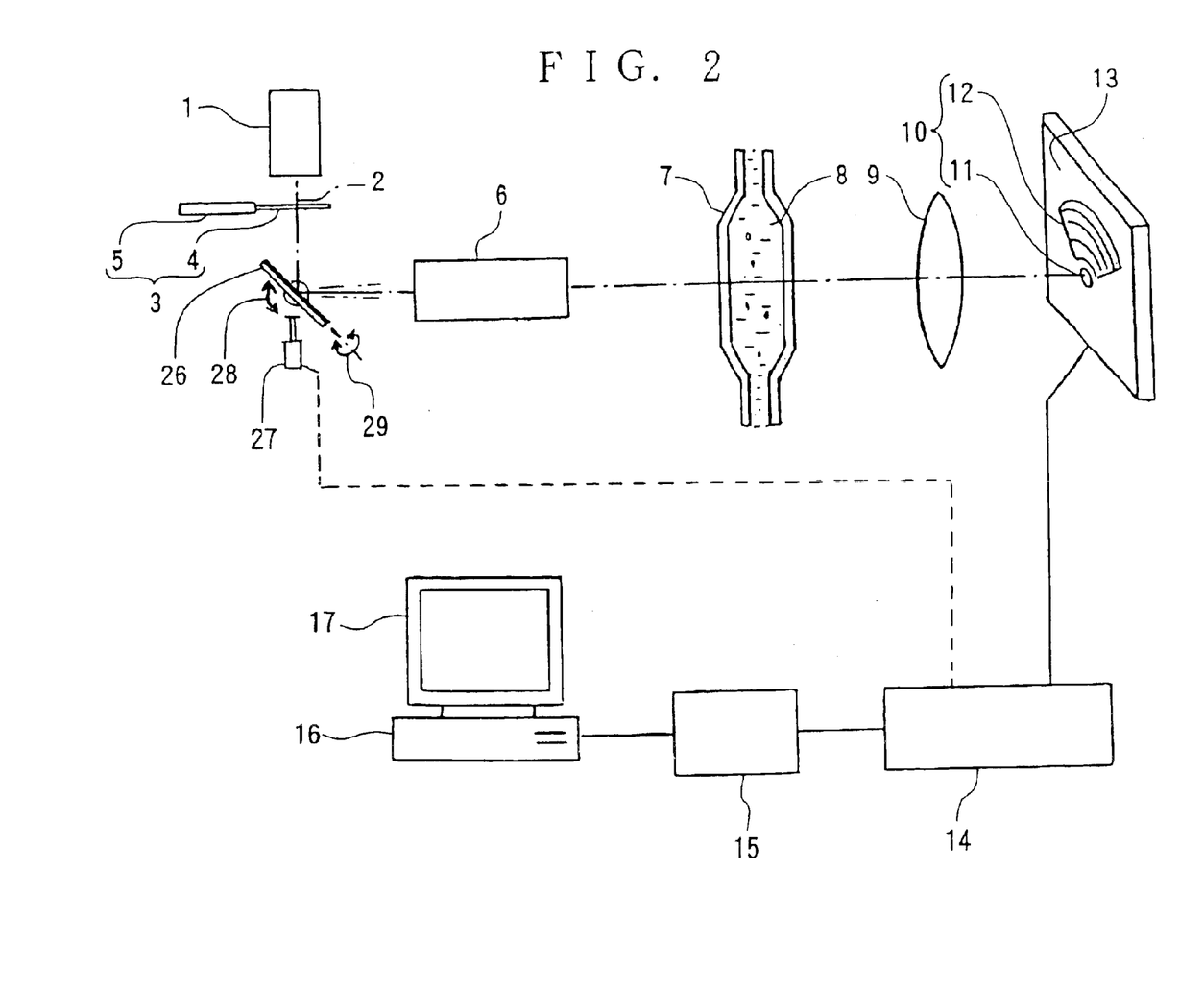
FIG. 2 is a view showing a second embodiment of the present invention.

FIG. 2 shows a second embodiment of the present invention in which a mirror 26 in communication with an optical axis adjusting mechanism 27 is provided. The mirror 26 directs the laser light 2 emitted from the light source 1 at a 90 degree angle into the beam expander 6. As shown, the optical axis adjusting mechanism 27, which is controlled by the CPU 15, is capable of moving the mirror 26 in the directions indicated by the arrows 28 and/or 29.

Figure 3:
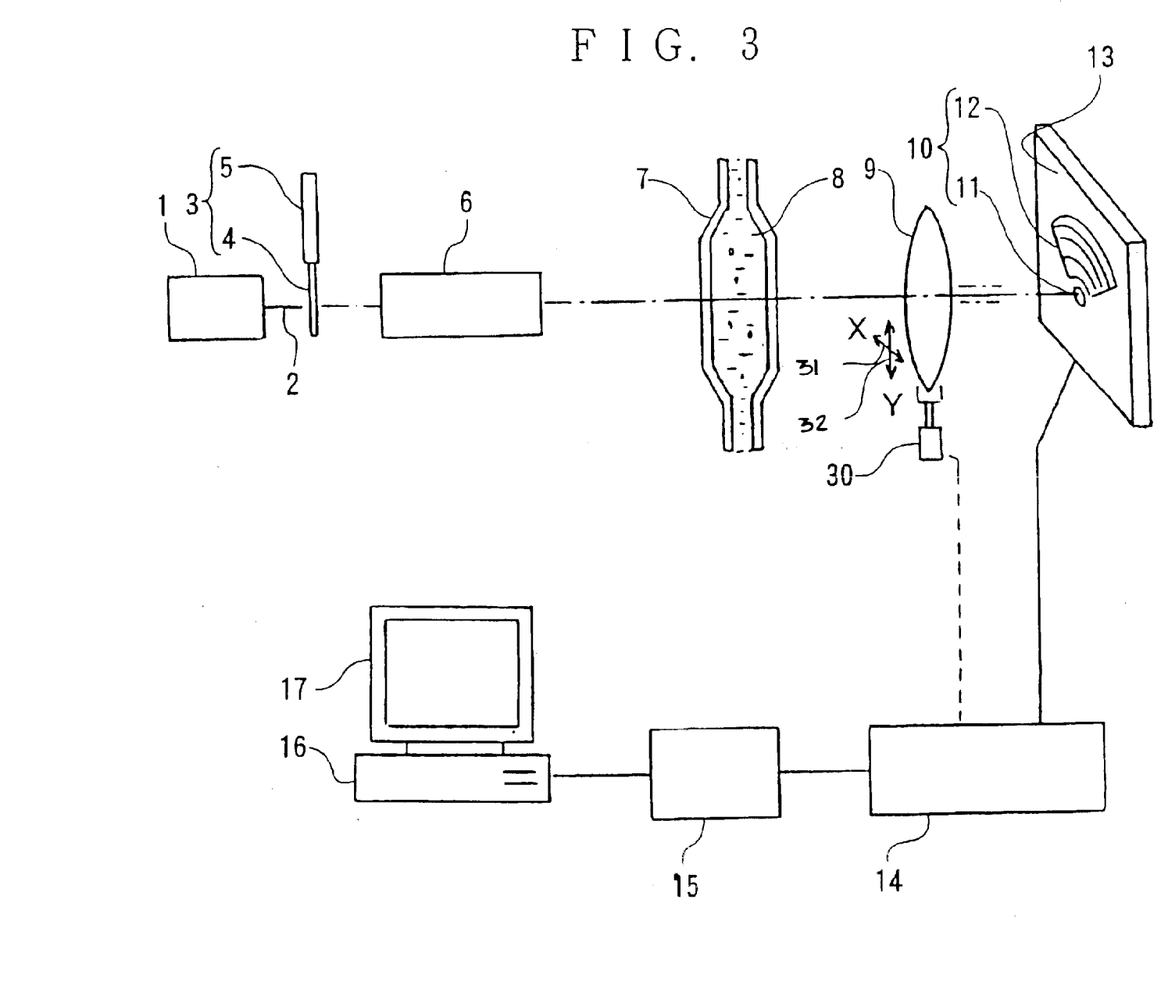
FIG. 3 is a view showing a third embodiment of the present invention.

FIG. 3 shows a third embodiment of the present invention in which an optical axis adjusting mechanism 30, which is controllable by the CPU 15, is provided. As shown in FIG. 3, the optical axis adjusting mechanism 30 is capable of moving the condenser lens 9 and the optical axis in X direction as indicated by the arrow 31 and/or in Y direction as indicated by the arrow 32.

Figure 4:
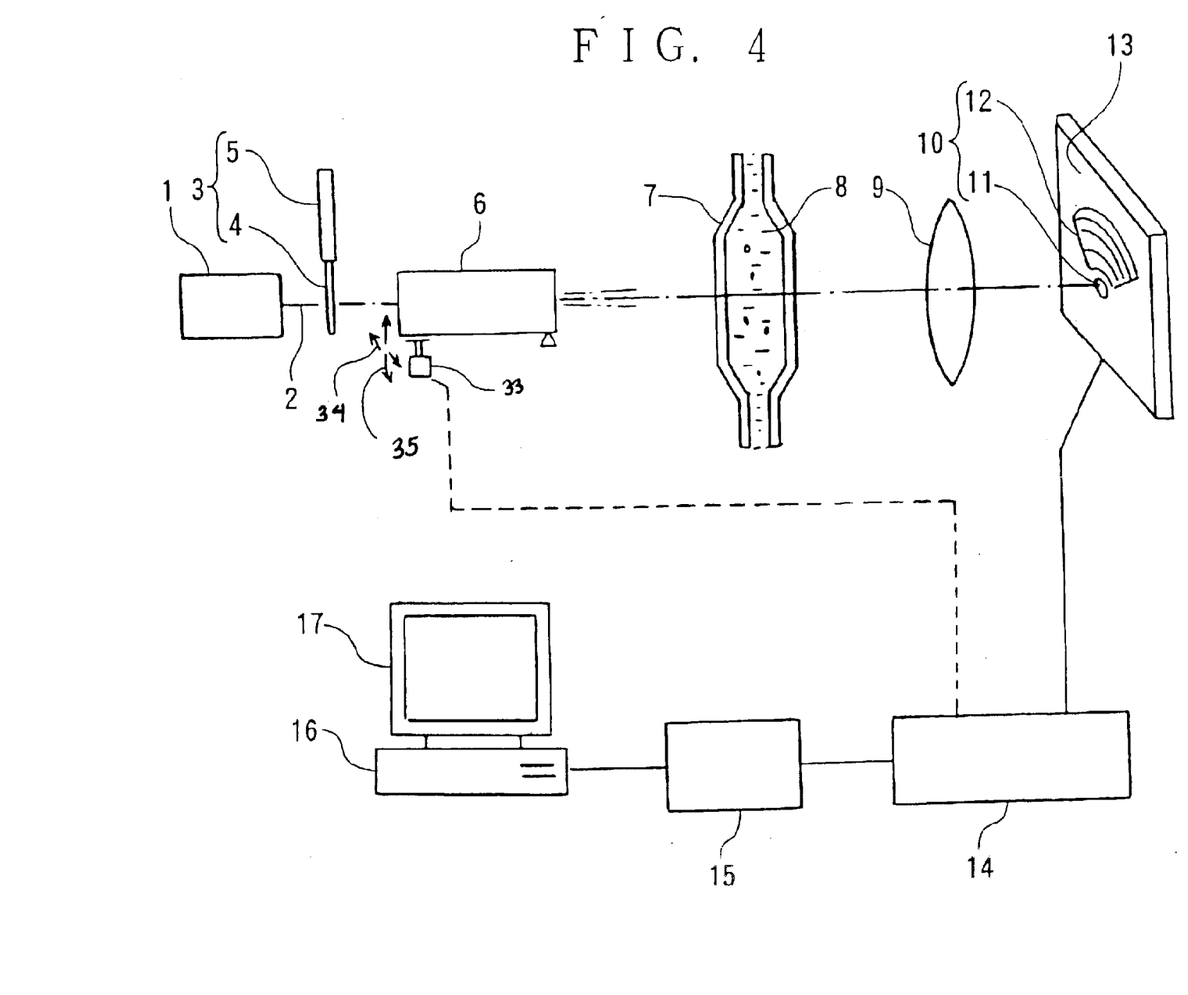
FIG. 4 is a view showing a fourth embodiment of the present invention.

FIG. 4 shows a fourth embodiment of the present invention in which an optical axis adjusting mechanism 33, which is in communication with the CPU 15, is provided. The optical axis adjustment mechanism 33 is capable of moving the beam expander 6 in the X direction as indicated by the arrow 34 and/or in Y direction as indicated by the arrow 35.

Figure 5:
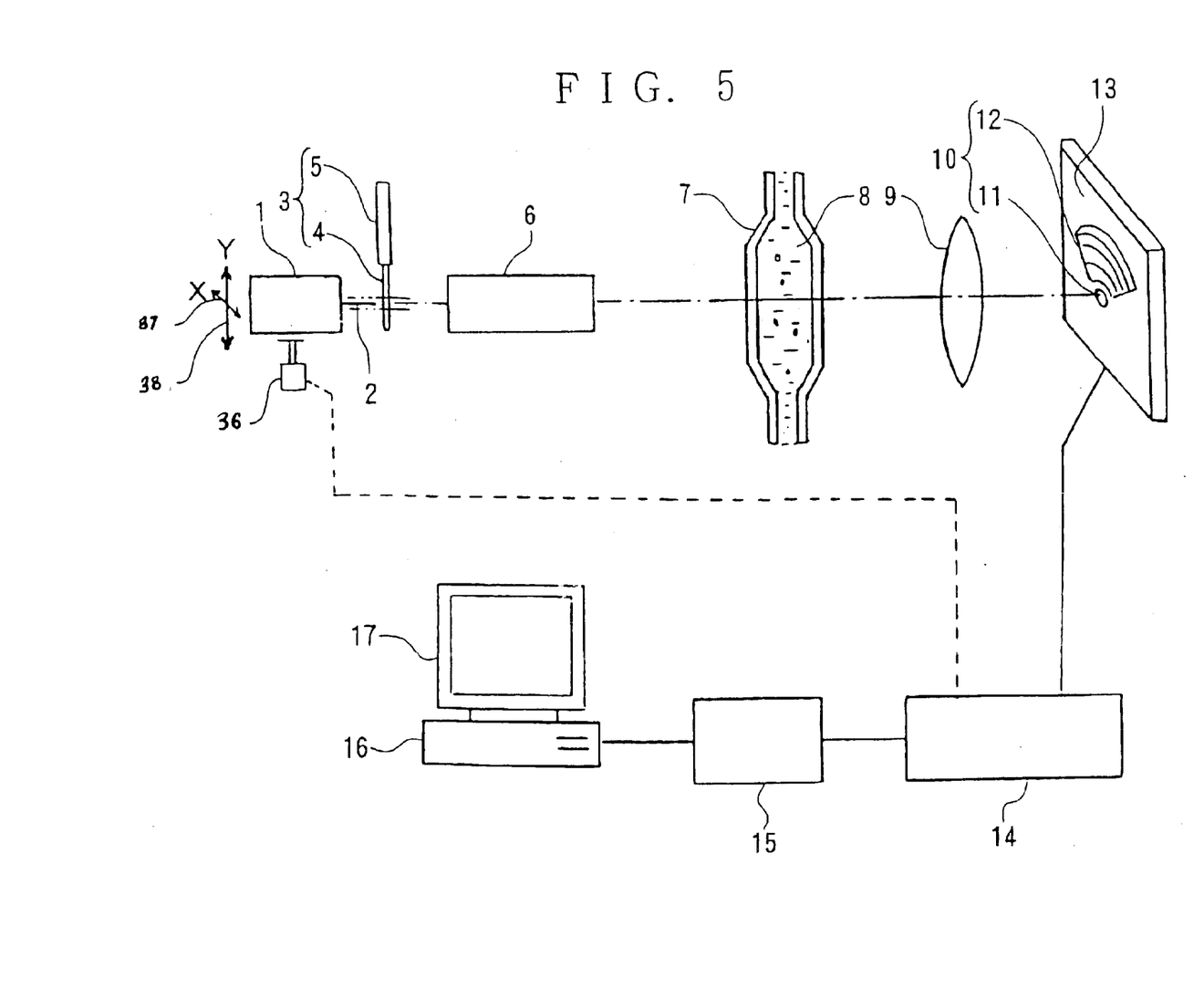
FIG. 5 is a view showing a fifth embodiment of the present invention.

FIG. 5 shows a fifth embodiment of the present invention in which an optical axis adjusting mechanism 36, which is controlled by the CPU 15, is provided. The optical axis adjusting mechanism 36 is capable of moving the light source 1 in the X direction as indicated by an arrow 37 and/or in the Y direction as indicated by an arrow 38.

Figure 6:
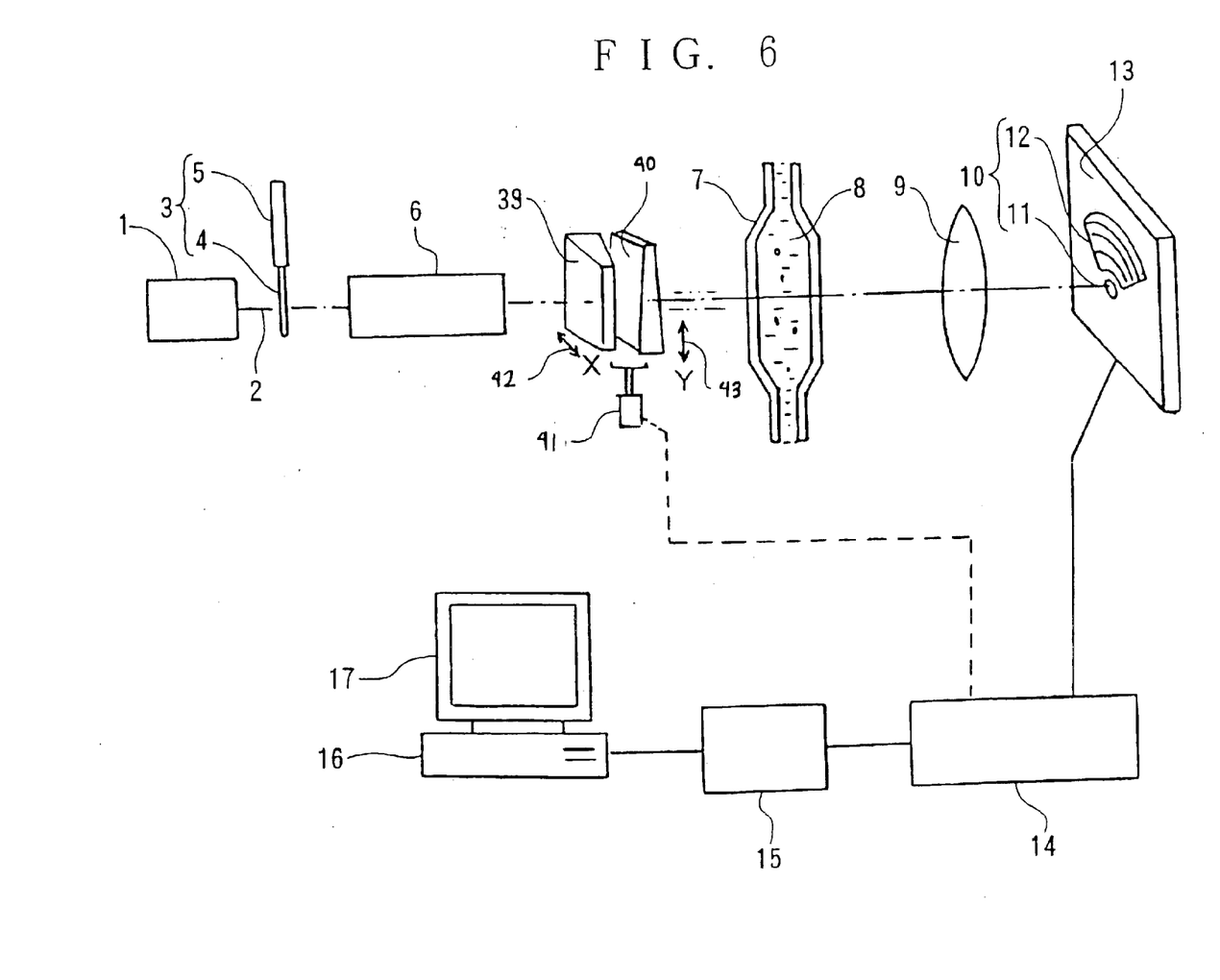
FIG. 6 is a view showing a sixth embodiment of the present invention.

FIG. 6 shows a sixth embodiment of the present invention in which cuneal prisms 39 and 40 are positioned between the beam expander 6 and the cell 7 within the propagation path of the laser light 2. As shown in FIG. 6, the cuneal prisms 39 and 40 are connected to an optical axis adjusting mechanism 41, which is in communication with the CPU 15. The optical axis mechanism 41 is capable of moving the cuneal prism 39 in the X direction as indicated by an arrow 42, capable of moving the cuneal prism 40 in the Y direction as indicated by an arrow 43.

The present invention further discloses a method of using the present invention to determine particle size. In the embodiments described above, the central positions of the light source 1 and the photodetector 10 are automatically adjusted to be in a state most suitable for measuring particle size within a sample 8. The embodiments described above provide various systems capable of monitoring quantity of light prior to irradiating a sample 8 and quantity of light transmitted through the sample 8 incident on a photodetector 10. In addition, the various embodiments of the present invention permit the user to easily adjust the position of a light source 1, a photodetector 10, or an optical device positioned between the light source 1 and the photodetector 10. In an alternate embodiment, the present invention may also be constructed such that the CPU 15 is capable of performing a control and monitor function for the system. In addition to monitoring the light intensities as various points in the system, the CPU 15 is capable of performing an error detection process. Exemplary errors include bubble contamination of a sample and system misalignment. In another embodiment, the measuring system disclosed herein may also be capable of determining an optimal control position to make a quantity of light fall in a controllable range on the photodetector 10. Additionally, the present invention is capable of storing the positions of various components, thereby enabling the system to reconstruct a previous experiment.

The present invention eliminates the burdensome manual optical axis adjustment currently required for every measurement in current systems. Furthermore, the present system permits the operator to maintain the system configuration best suited for a particular measurement. Accordingly, the present system enables the operator to perform measurements in an optimal condition while achieving a high degree of measuring precision.

To practice the first embodiment of the present invention, a diffraction device 18 is inserted into an optical path with the shutter 3 opened thereby creating an optical axis by using diffracted light produced by the diffraction device 18. Once the optical axis is created, the diffraction device 18 may be removed from the propagation path. The CPU 15, which is continuously receiving information relating to the position of the optical axis from the photodetector 10, controls the optical axis adjusting mechanism 19 based on the foregoing information, thereby ensuring the photodetector 10 is always in a condition best suited to measuring.

In the embodiment described above, the optical axis adjusting mechanism 19 is in communication with the photodetector 10 and controlled by the CPU 15. As shown in FIGS. 2 through 6, the present invention permits the user to control and monitor the optical axis with the CPU 15 by positioning the optical axis actuators in a plurality of locations. Accordingly, the operations for the optical axis adjustment in embodiments shown in FIGS. 2 to 6 are similar to that of the first embodiments shown in foregoing FIG. 1.

What is claimed is:

1. A light scattering particle size distribution measuring apparatus, comprising:
    a light source capable of emitting laser light;
    a light shutter modulating said laser light;
    a beam expander expanding said laser light;
    a material cell containing a material sample;
    a condenser lens capable of focusing transmitted and scattered light;
    a photodetector capable of receiving said scattered and transmitted light;
    at least one optical axis adjustment mechanism capable of automatically aligning and maintaining a central position of said photodetector with a central position of said light source;
    a multiplexer in communication with said photodetector and said optical axis adjustment mechanism; and
    a CPU in communication with said multiplexer and a personal computer, said CPU capable of providing control signals to said at least one optical axis adjustment mechanism based on a signal received from said photodetector.

2. The apparatus of claim 1, further comprising a mirror positioned between said light source and said light shutter.

3. The apparatus of claim 1, further comprising a first cuneal prisms and a second cuneal prism, wherein said first and second cuneal prisms positioned between said beam expander and said material cell.

4. The apparatus of claim 1 wherein said optical axis adjustment mechanism comprises an X-Y optical positioning stage.

5. The apparatus of claim 1 wherein said optical axis adjustment mechanism is in communication with at least one device selected from the group consisting of said light source, said mirror, said beam expander, said condensor lens, and said photodetector.

6. A light scattering particle size distribution measuring apparatus, which irradiates a sample with light from a light source, detects the resulting scattered light from the sample by a photodetector, and measures the size distribution of particles in the sample on the basis of a scattered light intensity pattern obtained, comprising a mechanism capable of automatically adjusting the central positions of the light source and the photodetector in a state most suitable for measuring by always monitoring quantity of light antecedent to irradiating a sample and quantity of light on a photodetector alter irradiating a sample and adjusting a position of a light source, a photodetector or an optical device between the light source and the photodetector.

7. A light scattering particle size distribution measuring apparatus, which irradiates a sample with light from a light source, detects the resulting scattered light from the sample by a photodetector, and measures the size distribution of particles in the sample on the basis of a scattered light intensity pattern obtained, comprising an optical axis adjustment mechanism capable of holding control data antecedent to a decrease of a quantity of light when the quantity of light on a photodetector is significantly lowered compared with a quantity of light antecedent to irradiating a sample by always monitoring the quantity of light antecedent to irradiating a sample and the quantity of light on a photodetector.

8. A method of using the scattering of light to measure the particle size distribution within a sample, comprising;
    irradiating a sample with light from a light source;
    detecting a resulting scattered light from the sample by a photodetector;
    monitoring a central position of the light source and the photodetector;
    monitoring a quantity of light antecedent to irradiating the sample and a quantity of light on the photodetector;
    measuring a size distribution of particles in the sample on the basis of a scattering light intensity pattern; and
    storing and retrieving an optimal position in a range of a quantity of light on a photodetector.

9. A method of using the scattering of light to measure the particle size distribution within a sample, comprising:
    irradiating a sample with light from a light source;
    detecting a resulting scattered light from the sample by a photodetector;
    monitoring a central position of the light source and the photodetector;
    monitoring a quantity of light antecedent to irradiating the sample and a quantity of light on the photodetector;
    measuring a size distribution of particles in the sample on the basis of a scattered light intensity pattern; and
    aligning and maintaining a central position of said photodetector with a central position of said light source with an automatic adjustment mechanism.

10. A light scattering particle size distribution measuring apparatus, comprising:
    a light source capable of emitting laser light;

a light shutter modulating said laser light;

a beam expander expanding said laser light;

a material cell containing a material sample;

a condensor lens capable of focusing transmitted and scattered light;

a photodetector capable of receiving said scattered and transmitted light;

at least one optical axis adjustment mechanism capable of automatically aligning and maintaining a central position of said photodetector with a central position of the said light source and configured to always monitor a quantity of light antecedent to irradiating the material sample and a quantity of light on the photodetector, wherein the optical axle adjustment mechanism comprises an X-Y optical positioning stage;

a multiplexer in communication with said photodetector and said optical axis adjustment mechanism; and a CPU in communication with said multiplexer and a personal computer, said CPU capable of providing control signals to said at least one optical axis adjustment mechanism based on a signal received from said photodetector.

* * * * *